(12) United States Patent
He et al.

(10) Patent No.: US 7,962,222 B2
(45) Date of Patent: Jun. 14, 2011

(54) BATTERY PROTECTION AND ZERO-VOLT BATTERY RECOVERY SYSTEM FOR AN IMPLANTABLE MEDICAL DEVICE

(75) Inventors: Yuping He, Northridge, CA (US); David L. Peterson, Saugus, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 580 days.

(21) Appl. No.: 11/550,872

(22) Filed: Oct. 19, 2006

(65) Prior Publication Data
US 2007/0129768 A1    Jun. 7, 2007

Related U.S. Application Data

(60) Provisional application No. 60/748,240, filed on Dec. 7, 2005.

(51) Int. Cl.
*A61N 1/08* (2006.01)
(52) U.S. Cl. .............. 607/61; 607/29; 607/33
(58) Field of Classification Search .......... 607/33, 607/61, 34
See application file for complete search history.

(56) References Cited

U.S. PATENT DOCUMENTS

| | | | | |
|---|---|---|---|---|
| 3,522,811 A | * | 8/1970 | Wingrove et al. | 607/27 |
| 3,867,950 A | * | 2/1975 | Fischell | 607/33 |
| 3,888,260 A | * | 6/1975 | Fischell | 607/36 |
| 3,942,535 A | * | 3/1976 | Schulman | 607/33 |
| 4,082,097 A | * | 4/1978 | Mann et al. | 607/33 |
| 4,947,844 A | * | 8/1990 | McDermott | 607/57 |
| 5,702,431 A | * | 12/1997 | Wang et al. | 607/61 |
| 5,713,939 A | * | 2/1998 | Nedungadi et al. | 607/33 |
| 5,733,313 A | | 3/1998 | Barreras, Sr. et al. | |
| 5,869,970 A | * | 2/1999 | Palm et al. | 324/433 |
| 5,925,068 A | * | 7/1999 | Kroll | 607/29 |
| 6,507,173 B1 | * | 1/2003 | Spiridon et al. | 320/162 |
| 6,553,263 B1 | * | 4/2003 | Meadows et al. | 607/61 |
| 6,778,856 B2 | * | 8/2004 | Connelly et al. | 607/32 |
| 7,177,691 B2 | * | 2/2007 | Meadows et al. | 607/36 |
| 7,184,836 B1 | * | 2/2007 | Meadows et al. | 607/33 |
| 7,248,929 B2 | * | 7/2007 | Meadows et al. | 607/61 |

(Continued)

OTHER PUBLICATIONS

U.S. Appl. No. 11/215,946, filed Aug. 30, 2005, Yan.

(Continued)

*Primary Examiner* — Niketa I Patel
*Assistant Examiner* — Hiba El-Kaissi
(74) *Attorney, Agent, or Firm* — Wong, Cabello, Lutsch, Rutherford & Brucculeri, LLP

(57) ABSTRACT

Circuitry useable to protect and reliably charge a rechargeable battery, even from a zero-volt state, is disclosed, and is particularly useful when employed in an implantable medical device. The circuit includes two charging paths, a first path for trickle charging the battery at a relatively low current when the battery voltage is below a threshold, and a second path for charging the battery at relatively higher currents that the battery voltage is above a certain threshold. A passive diode is used in the first trickle-charging path which allows trickle charging even when the battery voltage is too low for reliable gating, while a gateable switch (preferably a PMOS transistor) is used in the second higher-current charging path when the voltage is higher and the switch can therefore be gated more reliably. A second diode between the two paths ensures no leakage to the substrate through the gateable switch during trickle charging. The load couples to the battery through the switch, and preferably through a second switch specifically used for decoupling the load.

16 Claims, 8 Drawing Sheets

U.S. PATENT DOCUMENTS

| | | | |
|---|---|---|---|
| 7,295,878 B1 * | 11/2007 | Meadows et al. | 607/61 |
| 7,428,438 B2 * | 9/2008 | Parramon et al. | 607/61 |
| 2002/0133211 A1 * | 9/2002 | Weiner et al. | 607/61 |
| 2003/0191504 A1 * | 10/2003 | Meadows et al. | 607/33 |
| 2003/0195581 A1 * | 10/2003 | Meadows et al. | 607/29 |
| 2005/0131495 A1 * | 6/2005 | Parramon et al. | 607/61 |
| 2006/0217785 A1 * | 9/2006 | Matei | 607/61 |
| 2007/0060980 A1 * | 3/2007 | Strother et al. | 607/61 |
| 2007/0270922 A1 * | 11/2007 | Zierhofer et al. | 607/61 |

OTHER PUBLICATIONS

Data Sheet for Motorola Device No. MC33349, "Lithium Battery Protection Circuit for One Cell Battery Packs," (May 2000).

U.S. Appl. No. 11/177,503, filed Jul. 8, 2005, Peterson et al.

* cited by examiner

BATTERY PROTECTION AND ZERO-VOLT BATTERY RECOVERY SYSTEM FOR AN IMPLANTABLE MEDICAL DEVICE

CROSS-REFERENCE TO RELATED APPLICATIONS

This non-provisional patent application claims priority to U.S. Provisional Patent Application Ser. No. 60/748,240, filed Dec. 7, 2005, which is hereby incorporated by reference in its entirety.

FIELD OF THE INVENTION

The present invention relates generally to circuitry and techniques for battery protection and zero-Volt battery recovery preferably for use in an implantable medical device such as an implantable stimulator device, or more specifically an implantable pulse generator.

BACKGROUND

Implantable stimulation devices generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder sublaxation, etc. The present invention may find applicability in all such applications, although the description that follows will generally focus on the use of the invention within a Spinal Cord Stimulation (SCS) system, such as that disclosed in U.S. patent application Ser. No. 11/177,503, filed Jul. 8, 2005, which is incorporated herein by reference in its entirety.

Spinal cord stimulation is a well-accepted clinical method for reducing pain in certain populations of patients. An SCS system typically includes an Implantable Pulse Generator (IPG) or Radio-Frequency (RF) transmitter and receiver, electrodes, at least one electrode lead, and, optionally, at least one electrode lead extension. The electrodes, which reside on a distal end of the electrode lead, are typically implanted along the dura of the spinal cord, and the IPG or RF transmitter generates electrical pulses that are delivered through the electrodes to the nerve fibers within the spinal column. Individual electrode contacts (the "electrodes") are arranged in a desired pattern and spacing to create an electrode array. Individual wires within one or more electrode leads connect with each electrode in the array. The electrode lead(s) exit the spinal column and generally attach to one or more electrode lead extensions. The electrode lead extensions, in turn, are typically tunneled around the torso of the patient to a subcutaneous pocket where the IPG or RF transceiver is implanted. Alternatively, the electrode lead may directly connect with the IPG or RF transceiver. For examples of other SCS systems and other stimulation systems, see U.S. Pat. Nos. 3,646,940 and 3,822,708, which are hereby incorporated by reference in their entireties. Of course, implantable pulse generators are active devices requiring energy for operation, such as is provided by an implanted battery or an external power source.

As should be obvious, an IPG needs electrical power to function. Such power can be provided in several different ways, such as through the use of a rechargeable or non-rechargeable battery or through electromagnetic (EM) induction provided from an external charger, or from combinations of these and other approaches, which are discussed in further detail in U.S. Pat. No. 6,553,263 ("the '263 patent"), which is incorporated herein by reference in its entirety. Perhaps the favorite of these approaches is to use a rechargeable battery in the IPG, such as a lithium-ion battery or a lithium-ion polymer battery. Such a rechargeable battery can generally supply sufficient power to run an IPG for a sufficient period (e.g., a day or more) between recharging. Recharging can occur through the use of EM induction, in which EM fields are sent by an external charger to the IPG. Thus, when the battery needs recharging, the patient in which the IPG is implanted can activate the external charger to percutaneously (i.e., through the patient's flesh) charge the battery (e.g., at night when the patient is sleeping or during other convenient periods).

The basics of such a system are shown in FIG. 1, which is largely descriptive of salient contents of the '263 patent. As shown, the system comprises in relevant part the external charger 208 and IPG 100. As noted, a coil 279 in the charger 208 produces an EM field 290 capable of percutaneous transmission through a patient's flesh 278. The external charger 208 may be powered by any known means, such as via a battery or by plugging into a wall outlet, for example. The EM field 290 is met at the IPG 100 by another coil 270, and accordingly an AC voltage is induced in that coil 270. This AC voltage is turn is rectified to a DC voltage at a rectifier 682, which may comprise a standard bridge circuit. (There may additionally be data telemetry associated with the EM field 290, but this detail is ignored as impertinent to the present disclosure). The rectified DC voltage is in turn sent to a charge controller 684, which operates generally to regulate the DC voltage and to produce either a constant voltage or constant current output as necessary for recharging the battery 180. The output of the charge controller 684, i.e., how aggressively the charge controller charges the battery 180, is dependent on the battery voltage, Vbat, as will be explained in further detail later. (The charge controller 684 can also be used to report the battery 180's charge status back to the external charge 208 via back telemetry using coil 270, as disclosed in the '263 application; however, because this function is not particularly relevant to this disclosure, it is not further discussed).

The output of the charge controller 684 is in turn met by two switches 701, 702 which respectively prevent the battery 180 from over-charging or over-discharging. As shown, these transistors are N-channel transistors, which will be "on," and thus capable of connecting the charge controller 684's output to the battery 180 when their gates are biased. Control of these gates is provided by a battery protection circuit 686, which receives the battery current and voltage, Ibat and Vbat, as control signals, again as will be explained in further detail later. For example, whenever the battery 180 exhibits too high a voltage, the battery protection circuit 686 will turn off the gate of the over-charging transistor 701 to protect the battery from further charging. A fuse positioned between the transistors 701, 702 and the battery 180 may also be used to further protect the battery from very high current events (not shown). The battery 180 is coupled to one of several loads in the IPG 100, such as the electrode stimulation circuitry, i.e., the circuits the battery 180 ultimately powers. The battery 180 is coupled to such loads through a load switch 504, which can isolate the battery 180 from the load to protect one from adverse effects of the other. This load switch 504 is preferably part of the charge controller 684, which may comprise its own integrated circuit, although this is not strictly necessary.

As discussed in the above-referenced '263 patent, the charging circuitry 684 can charge the battery 180 in different ways, depending on the status of the battery voltage, Vbat. Without reiterating the contents of that disclosure, such selective charging of the battery 180 is beneficial for safely charging the battery, particularly when a lithium-ion-based battery is used. Essentially, this safe charging scheme charges the battery 180 with smaller currents when the battery voltage Vbat is significantly depleted, and charges with higher currents when the battery voltage is still undercharged but at higher, safer levels.

Consider an embodiment in which Vbat=4.2V represents a nominal voltage for the battery 180. When Vbat<2.5V, the charge controller 684 will "trickle" charge the battery 180 with a low level current, e.g., Ibat=10 mA. As the battery charges and as Vbat increases, higher charging current can be used. For example, once Vbat>2.5V, a charging current of Ibat=50 mA may be set by the charge controller 684. Once the nominal voltage of 4.2V is approached, the charge controller 684 may continue to charge the battery 180 by providing a constant voltage instead of constant current on its output, which as charging continues is manifest in a gradual decay of the battery current. The relationship between Vbat and Ibat during battery charging is graphically illustrated in FIG. 2. Of course, these various current and voltage values are merely exemplary, and other parameters may be suitable depending on the system at hand. Also, more than two levels of charging current (e.g., 10 mA, 25 mA, and 50 mA) can be used in stair-step fashion.

As noted earlier, the battery protection circuit 686 prevents the battery from potential damage during charging by disconnecting the battery from the charge controller 684. Specifically, Vbat exceeds a safe value (e.g., greater than 4.2V), then the over-charging transistor 701 is disabled by the battery protection circuit 686 to block further charging. Likewise, if the battery voltage is less than a predetermined value and if Ibat exceeds a predetermined value, over-discharge transistor 702 is disabled to prevent discharging of the battery. While disclosed as controlling two transistors 701, 702, the battery protection circuit 686 may control a single disabling protection transistor which functions to disable the battery 180 during both over-charging and over-discharging. Load switch 504 may be similarly controlled to isolate the components to protect them from adverse voltages and currents.

While the charging and protection circuitry of FIG. 1 is suitable, its functionality may be hampered at extremely low battery voltages. As the '263 patent explains, this is because the battery protection circuit 686 is powered by the battery voltage, Vbat, and hence when Vbat is extremely low (e.g., approaching zero Volts), the battery protection circuitry 686 may not function as desired. In this regard, note that when Vbat is extremely low, and thus when the battery 180 is in need of charging, the battery protection circuit 686 needs to be able to turn transistors 701 and 702 on, else the charging controller 684 will not be able to pass a charging current, Ibat, to the battery. However, when Ibat is low, the battery protection circuit 686 may have difficulty generating a sufficient voltage to turn on the gates of the N-channel transistors 701 and 702. Specifically, the battery protection circuitry 686 must be able to produce a gate voltage for the transistors that is greater than Vgs (i.e., the potential difference between the gate and source of the transistors). In short, the battery protection circuitry needs to be able to produce a gate voltage which exceeds a threshold voltage (Vt) of the transistors given the source voltages apparent at the transistors. If Vbat is below this threshold voltage, the battery protection circuit 686 may not be able to produce a suitably-high gate voltage to turn transistors 701 and 702 on.

Should this occur, the battery 180 cannot be charged, even though Vbat is low and hence the battery 180 is very much in need of charging. In other words, the charging and protection circuitry in FIG. 1 is potentially susceptible to failure at when Vbat is extremely low, i.e., at zero Volts or near-zero Volts. In a worst case this would mean that the IPG 100 is unrecoverable, and if implanted in a patient, may require the drastic step of surgical removal and replacement of the device. But this is unfortunate, because patients in which IPGs are implanted cannot necessarily be relied upon to diligently charge their implanted devices, and hence the risk of a depleted, unrecoverable battery is very real.

As a result, improved circuitry and techniques for protection and zero-Volt recovery for batteries in implantable medical devices would be beneficial. Such solutions are provided herein.

SUMMARY

Circuitry useable to protect and reliably charge a rechargeable battery, even from a zero-volt state, is disclosed, and is particularly useful when employed in an implantable medical device. The circuit includes two charging paths, a first path for trickle charging the battery at a relatively low current when the battery voltage is below a threshold, and a second path for charging the battery at relatively higher currents that the battery voltage is above a certain threshold. A passive diode is used in the first trickle-charging path which allows trickle charging even when the battery voltage is too low for reliable gating, while a gateable switch (preferably a PMOS transistor) is used in the second higher-current charging path when the voltage is higher and the switch can therefore be gated more reliably. A second diode between the two paths ensures no leakage to the substrate through the gateable switch during trickle charging. The load couples to the battery through the switch, and preferably through a second switch specifically used for decoupling the load.

BRIEF DESCRIPTION OF THE DRAWINGS

The above and other aspects of the present invention will be more apparent from the following more particular description thereof, presented in conjunction with the following drawings wherein.

DETAILED DESCRIPTION

The following description is of the best mode presently contemplated for carrying out the invention. This description is not to be taken in a limiting sense, but is made merely for the purpose of describing the general principles of the invention. The scope of the invention should be determined with reference to the claims and their equivalents.

Before discussing the battery protection and zero-Volt recovery aspects of the invention that is the focus of this disclosure, the circuitry, structure, and function of an implantable stimulator device in which the disclosed circuitry and technique can be used is set forth for completeness with respect to FIGS. 3-6. The disclosed implantable stimulator device may comprise implantable pulse generator (IPG), or similar electrical stimulator and/or electrical sensor, that may be used as a component of numerous different types of stimulation systems. More specifically, the description that follows relates to use of the invention within a spinal cord stimulation (SCS) system as an exemplary embodiment. However, it is to be understood that the invention is not so limited. Rather, the invention may be used with any type of implantable electrical circuitry that could benefit from improved battery protection and zero-Volt recovery techniques. For example, the present invention may be used as part of a pacemaker, an implantable pump, a defibrillator, a cochlear stimulator, a retinal stimulator, a stimulator configured to produce coordinated limb movement, a cortical or deep brain stimulator, or in any other stimulator configured to treat urinary incontinence, sleep apnea, shoulder sublaxation, etc. Moreover the technique can be used in non-medical and/or non-implantable devices or systems as well, i.e., in any device or system in which zero-Volt battery recovery and/or protection is necessary or desirable.

Figure 3:
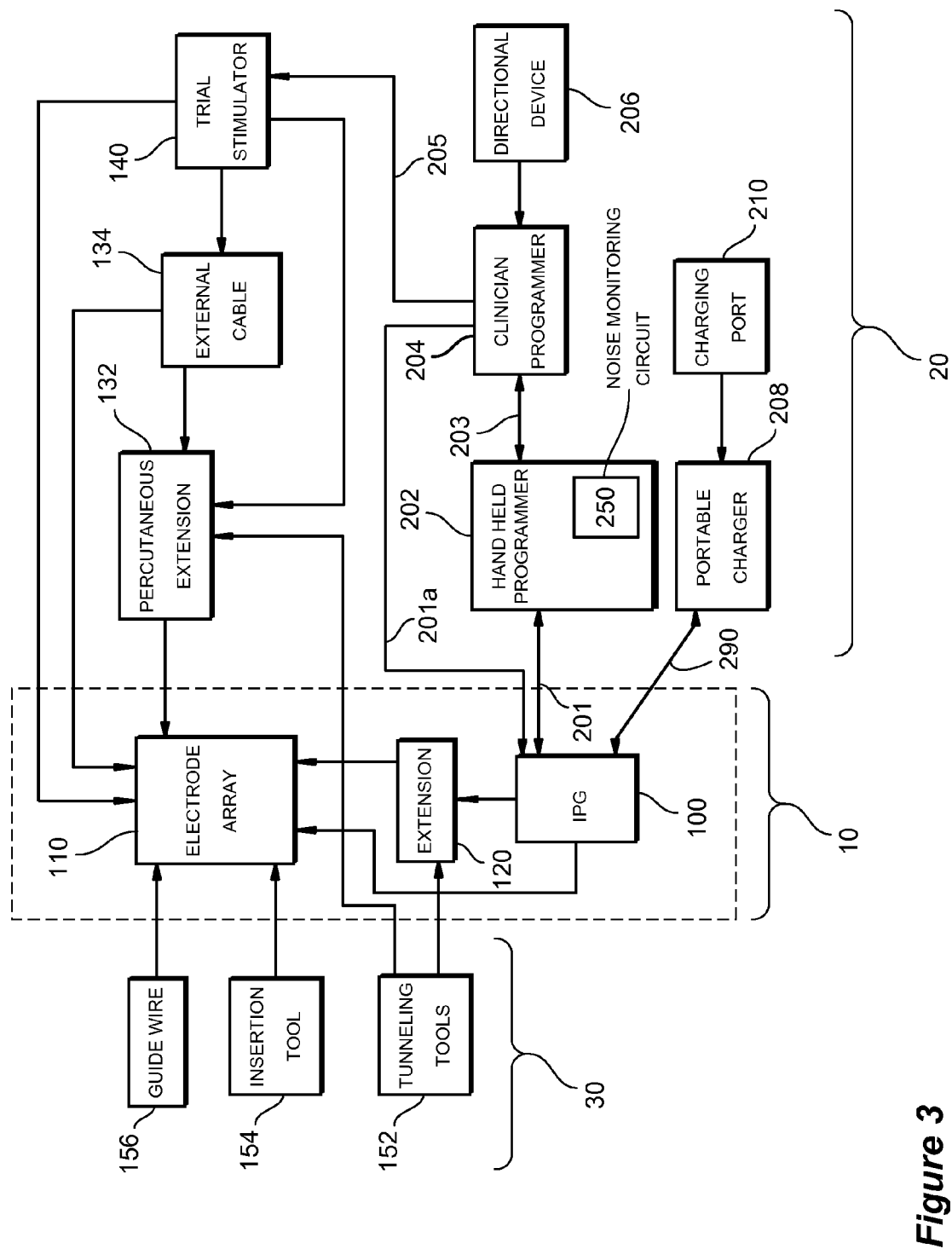
FIG. 3 shows a block diagram that illustrates exemplary implantable, external, and surgical components of a spinal cord stimulation (SCS) system that employs an implantable stimulator device in accordance with the present invention.

Turning first to FIG. 3, a block diagram is shown that illustrates the various components of an exemplary SCS system in which the invention may be used. These components may be subdivided into three broad categories: implantable components 10, external components 20, and surgical components 30. As seen in FIG. 3, the implantable components 10 include an implantable pulse generator (IPG) 100, an electrode array 110, and (as needed) a lead extension 120. The extension 120 may be used to electrically connect the electrode array 110 to the IPG 100. In an exemplary embodiment, the IPG 100, described more fully below in connection with FIG. 5 or 6, may comprise a rechargeable, multi-channel, telemetry-controlled, pulse generator housed in a rounded high-resistivity titanium alloy case to reduce eddy current heating during the inductive charging process. The IPG 100 may provide electrical stimulation through a multiplicity of electrodes, e.g., sixteen electrodes $E_1$ through $E_{16}$, included within the electrode array 110.

In this regard, the IPG 100 may include stimulating electrical circuitry ("stimulating electronics"), a power source, e.g., a rechargeable battery, and a telemetry system, the latter of which is particularly relevant to embodiments of the disclosed invention. Typically, the IPG 100 is placed in a surgically-made pocket either in the abdomen, or just at the top of the buttocks. It may, of course, also be implanted in other locations of the patient's body. Once implanted, the IPG 100 is connected to the lead system, comprising the lead extension 120, if needed, and the electrode array 110. The lead extension 120, for example, may be tunneled up to the spinal column. Once implanted and any trial stimulation period is complete, the lead system 110 and lead extension 120 are intended to be permanent. In contrast, the IPG 100 may be replaced if it fails.

Figure 4:
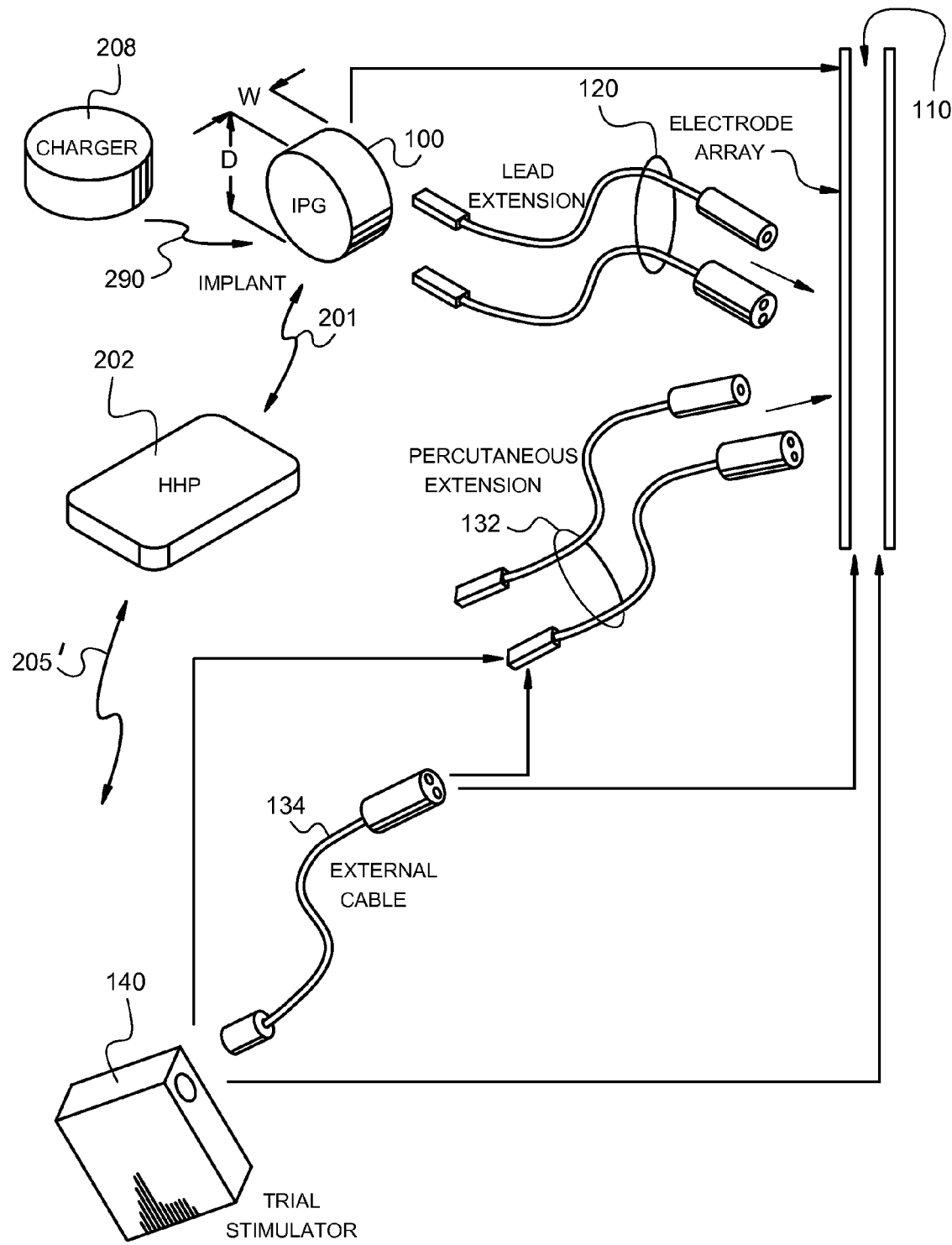
FIG. 4 shows various components of the SCS system of FIG. 1.

As seen best in FIG. 4, and as also illustrated in FIG. 3, the electrode array 110 and its associated lead system typically interface with the implantable pulse generator (IPG) 100 via the lead extension system 120 just mentioned. The electrode array 110 may also be connected to an external trial stimulator 140, through the use of a percutaneous lead extension 132 and/or an external cable 134. The external trial stimulator 140 typically includes the same or similar pulse generation circuitry as does the IPG 100, and is used on a trial basis, e.g., for 7-10 days, after the electrode array has been implanted and prior to implantation of the IPG 100, to test the effectiveness of the stimulation that is to be provided.

Still with reference to FIGS. 3 and 4, and as noted earlier, a hand-held programmer (HHP) 202 may be used to control the IPG 100 via a suitable non-invasive communications link 201, e.g., an RF link. Such control allows the IPG 100 to be turned on or off, and generally allows stimulation parameters, e.g., pulse amplitude, width, and rate, to be set by a patient or clinician within prescribed limits. The HHP 202 may also be linked with the external trial stimulator 140 through another link 205', e.g., an infra red link. Detailed programming of the IPG 100 is preferably accomplished through the use of an external clinician's programmer (CP) 204 (FIG. 3), which may also be hand-held and which may be coupled to the IPG 100 directly via link 201a or indirectly through the HHP 202. An external charger 208, non-invasively coupled with the IPG 100 through link 290, e.g., an inductive link, allows energy stored or otherwise made available to the charger 208 to be coupled into the rechargeable battery 180 housed within the IPG 100, as explained in the Background.

Figure 5:
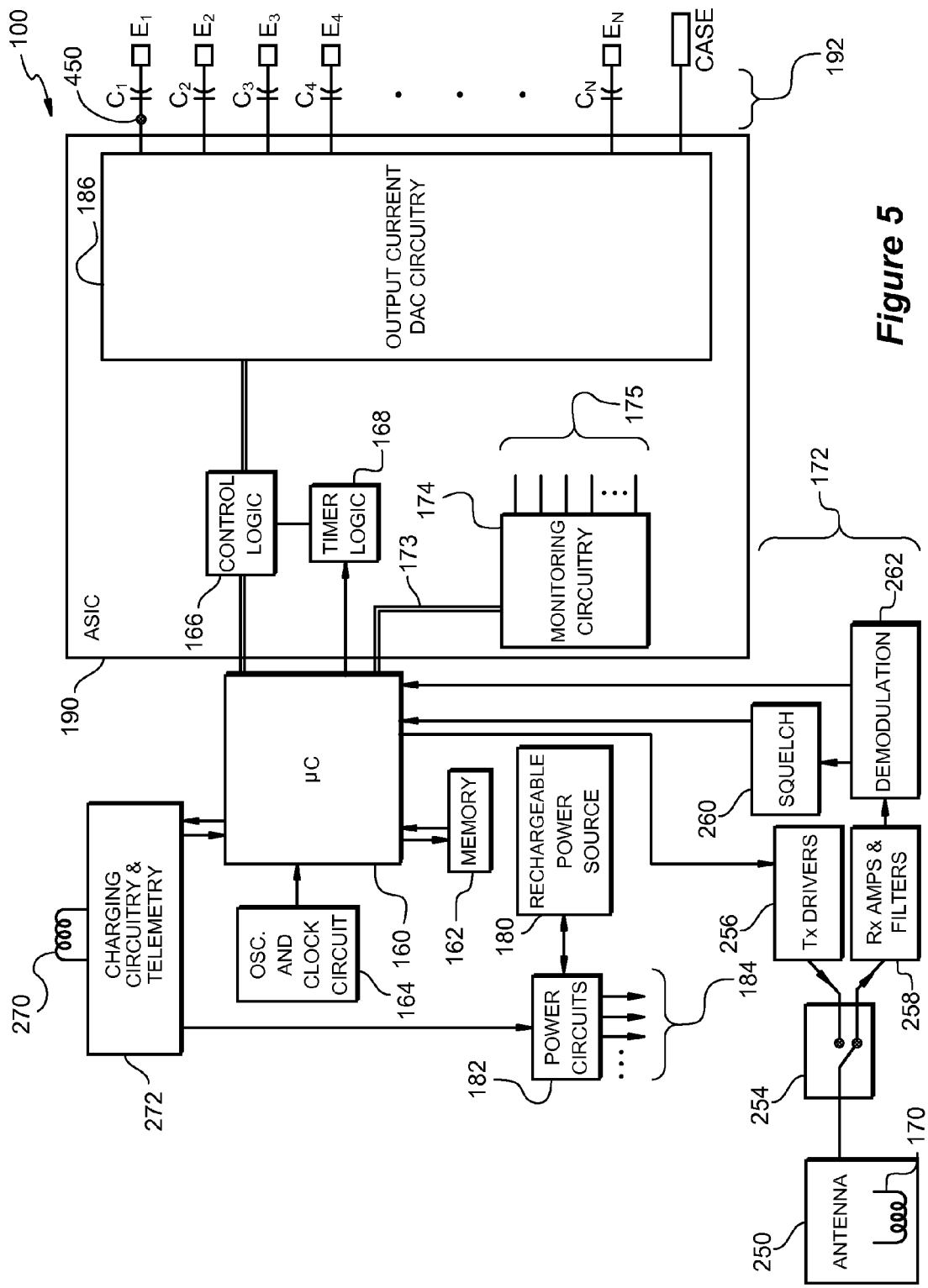
FIG. 5 shows a block diagram that illustrates the main components of one embodiment of an implantable stimulator device in which the invention can be used.

Turning next to FIG. 5, a block diagram is shown that illustrates the main components of one embodiment of an implantable pulse generator (IPG) 100 in which embodiments of the invention may be used. As seen in FIG. 5, the IPG includes a microcontroller (μC) 160 connected to memory circuitry 162. The μC 160 typically comprises a microprocessor and associated logic circuitry, which in combination with control logic circuits 166, timer logic 168, and an oscillator and clock circuit 164, generate the necessary control and status signals which allow the μC 160 to control the operation of the IPG in accordance with a selected operating program and stimulation parameters. (A "microcontroller" as used herein should be understood as any integrated device capable of processing signals in the IPG, including traditional microcontrollers, microprocessors, or other signal processors, including those that are application-specific, such as ASIC chips).

The operating program and stimulation parameters are telemetered to the IPG 100, where they are received via antenna 250 (which may include a coil 170 and/or other antenna components), processed, e.g., via RF-telemetry circuitry 172, and may be stored, e.g., within the memory 162. As noted earlier, the RF-telemetry circuitry 172 demodulates the signal it receives from the HHP 202 or CP 204 to recover the operating program and/or the stimulation parameters. More specifically, signals received by the antenna 250 are passed through the transmit/receive switch 254 to amplifiers and filters 258. From there, the received signals are demodulated (262) using Frequency Shift Keying (FSK) demodulation for example, and the data is then sent to the microcontroller 160 for processing and/or eventual storage. When RF-telemetry circuitry 172 is used to transmit information to the HHP 202 or CP 204 to report in some fashion on its status, the microcontroller 160 sends relevant data to transmission drivers 256, where the carrier is modulated by the data and amplified for transmission. The transmit/receive switch 254 would then be set to communicate with the transmission drivers 256, which in turn drive the data to the antenna 250 to be broadcast.

The microcontroller 160 is further coupled to monitoring circuits 174 via bus 173. The monitoring circuits 174 monitor the status of various nodes or other points 175 throughout the IPG 100, e.g., power supply voltages, current values, temperature, the impedance of electrodes attached to the various electrodes $E_1 \ldots E_N$, and the like. Informational data sensed through the monitoring circuit 174 may be sent to a remote location external to the IPG (e.g., a non-implanted location) through telemetry circuitry 172 via coil 170.

The operating power for the IPG 100 may be derived from a rechargeable power source 180, which may comprise a lithium-ion or lithium-ion polymer battery, for example, as discussed earlier. The rechargeable battery 180 provides an unregulated voltage to power circuits 182. The power circuits 182, in turn, generate the various voltages 184, some of which are regulated and some of which are not, as needed by the various circuits located within the IPG 100. In a preferred embodiment, the battery 180 is charged by an electromagnetic field created by an external portable charger 208 (FIGS. 1, 3) as already noted. When placed near the IPG 100 (e.g., centimeters away), an electromagnetic field emanating from the portable charger 208 induces a current in charging coil 270 (even through a patient's skin). This current is then rectified and regulated to charge the battery 180, as explained in the Background. Further associated with the charging circuitry is charging telemetry circuitry 272, which is used for example by the IPG 100 to report back to the portable charger 208 when the battery is full, and thus when portable charger can be shut off.

In one exemplary embodiment, any of the N electrodes may be assigned to up to k possible groups or "channels." In one preferred embodiment, k may equal four. Moreover, any of the N electrodes can operate, or be included in, any of the k channels. The channel identifies which electrodes are selected to synchronously source or sink current to create an electric field in the tissue to be stimulated. Amplitudes and polarities of electrodes on a channel may vary, e.g., as controlled by the HHP 202. External programming software in the CP 204 is typically used to set parameters including electrode polarity, amplitude, pulse rate and pulse width for the electrodes of a given channel, among other possible programmable features.

The N programmable electrodes can be programmed to have a positive (sourcing current), negative (sinking current), or off (no current) polarity in any of the k channels. Moreover, each of the N electrodes can operate in a bipolar mode or multipolar mode, e.g., where two or more electrode contacts are grouped to source/sink current at the same time. Alternatively, each of the N electrodes can operate in a monopolar mode where, e.g., the electrode contacts associated with a channel are configured as cathodes (negative), and the case electrode (i.e., the IPG case) is configured as an anode (positive).

Further, the amplitude of the current pulse being sourced or sunk to or from a given electrode contact may be programmed to one of several discrete current levels, e.g., between 0 to 10 mA in steps of 0.1 mA. Also, the pulse width of the current pulses is preferably adjustable in convenient increments, e.g.,
from 0 to 1 milliseconds (ms) in increments of 10 microseconds (µs). Similarly, the pulse rate is preferably adjustable within acceptable limits, e.g., from 0 to 1000 Hz. Other programmable features can include slow start/end ramping, burst stimulation cycling (on for X time, off for Y time), and open or closed loop sensing modes.

The stimulation pulses generated by the IPG 100 may be charge balanced. This means that the amount of positive charge associated with a given stimulus pulse is offset with an equal and opposite negative charge. Charge balance may be achieved through coupling capacitors $C_x$, which provide a passive capacitor discharge that achieves the desired charge-balanced condition. Alternatively, active biphasic or multiphasic pulses with positive and negative phases that are balanced may be used to achieve the needed charge balanced condition.

In short, the IPG 100 is able to individually control the currents at the N electrodes. Controlling the output current Digital-to-Analog Current (DAC) circuitry 186 using the microcontroller 160, in combination with the control logic 166 and timer logic 168, allows each electrode contact to be paired or grouped with other electrode contacts, including the monopolar case electrode, to control the polarity, amplitude, rate, pulse width and channel through which the current stimulus pulses are provided.

As shown in FIG. 5, much of circuitry included within the IPG 100 may be realized on a single application specific integrated circuit (ASIC) 190. This allows the overall size of the IPG 100 to be quite small, and readily housed within a suitable hermetically-sealed case. The IPG 100 may include N feedthroughs to allow electrical contact to be individually made from inside of the hermetically-sealed case with the N electrodes that form part of the lead system outside of the case.

As noted earlier, in use, the IPG 100 may be placed in a surgically-made pocket, e.g., in the abdomen or just at the top of the buttocks, and detachably connected to the lead system (comprising optional lead extension 120 and electrode array 110). While the lead system is intended to be permanent, the IPG 100 may be replaced should it fail.

The telemetry features of the IPG 100 allow the status of the IPG to be checked. For example, when the HHP 202 and/or the CP 204 initiate a programming session with the IPG 100, the capacity of the battery is telemetered so that the external programmer can calculate the estimated time to recharge. Any changes made to the current stimulus parameters are confirmed through back-telemetry, thereby assuring that such changes have been correctly received and implemented within the implant system. Moreover, upon interrogation by the external programmer, all programmable settings stored within the implant system 10 may be uploaded to one or more external programmers.

Figure 6:
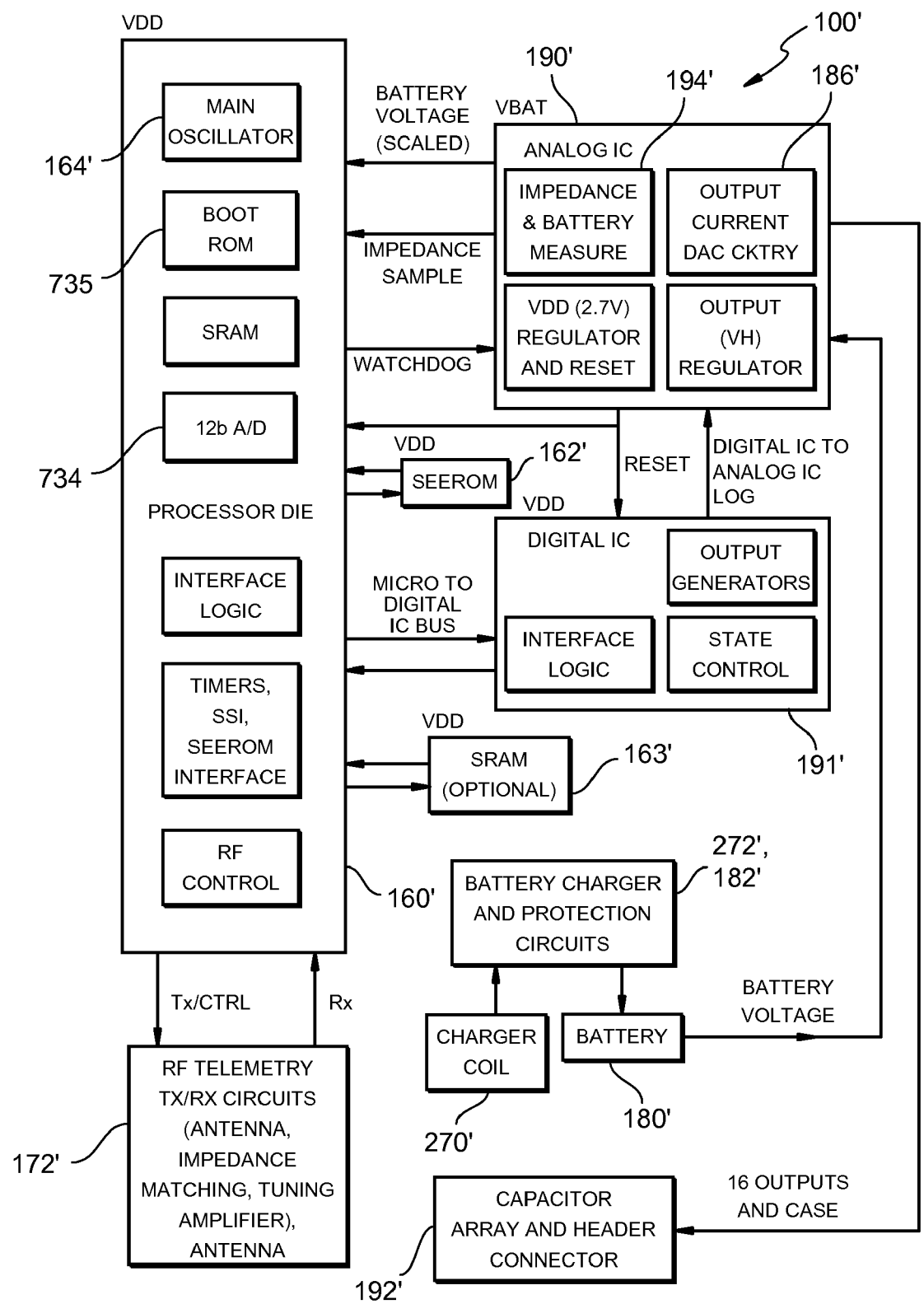
FIG. 6 shows a block diagram that illustrates another embodiment of an implantable stimulator device in which the invention can be used.

Turning next to FIG. 6, a hybrid block diagram of an alternative embodiment of an IPG 100' that may be used with the invention is illustrated. The IPG 100' includes both analog and digital dies, or integrated circuits (ICs), which may be housed in a single hermetically-sealed rounded case having, for instance, a diameter of about 45 mm and a maximum thickness of about 10 mm. Many of the circuits contained within the IPG 100' are identical or similar to the circuits contained within the IPG 100, shown in FIG. 5. The IPG 100' includes a processor die, or chip, 160', an RF telemetry circuit 172' (typically realized with discrete components), a charger coil 270', a rechargeable battery 180', battery charger and protection circuits 272', 182', memory circuits 162' (SEEPROM) and 163' (SRAM), a digital IC 191', an analog IC 190', and a capacitor array and header connector 192'.

The capacitor array and header connector 192' include sixteen output decoupling capacitors, as well as respective feed-through connectors for connecting one side of each decoupling capacitor through the hermetically-sealed case to a connector to which the electrode array 110, or lead extension 120, may be detachably connected.

The processor 160' may be realized with an application specific integrated circuit (ASIC), field programmable gate array (FPGA), or the like that comprises a main device for full bi-directional communication and programming. The processor 160' may utilize an 8086 core (the 8086 is a commercially-available microprocessor available from, e.g., Intel), or a low power equivalent thereof, SRAM or other memory, two synchronous serial interface circuits, a serial EEPROM interface, and a ROM boot loader 735. The processor die 160' may further include an efficient clock oscillator circuit 164', and (as noted earlier) mixer and modulator/demodulator circuitry implementing the QFAST RF telemetry method. An analog-to-digital converter (A/D) circuit 734 is also resident on the processor 160' to allow monitoring of various system level analog signals, impedances, regulator status and battery voltage. The processor 160' further includes the necessary communication links to other individual ASICs utilized within the IPG 100'. The processor 160', like all similar processors, operates in accordance with a program that is stored within its memory circuits.

The analog IC (AIC) 190' may comprise an ASIC that functions as the main integrated circuit that performs several tasks necessary for the functionality of the IPG 100', including providing power regulation, stimulus output, and impedance measurement and monitoring. Electronic circuitry 194' performs the impedance measurement and monitoring function.

The analog IC 190' may also include output current DAC circuitry 186' configured to supply current to a load, such as tissue, for example. The output current DAC circuitry 186' may be configured to deliver up to 20 mA aggregate and up to 12.7 mA on a single channel in 0.1 mA steps. However, it will be noted that the output current DAC circuitry 186' may be configured to deliver any amount of aggregate current and any amount of current on a single channel, according to one exemplary embodiment.

Regulators for the IPG 100' supply the processor and the digital sequencer with a voltage. Digital interface circuits residing on the analog IC 190' are similarly supplied with a voltage. A programmable regulator supplies the operating voltage for the output current DAC circuitry 186'. The coupling capacitors $C_x$ and electrodes $E_x$, as well as the remaining circuitry on the analog IC 186', may all be housed within the hermetically sealed case of the IPG 100. A feedthrough pin, which is included as part of the header connector 192', allows electrical connection to be made between each of the coupling capacitors $C_N$ and the respective electrodes $E_1$, $E_2$, $E_3$, ..., or $E_{16}$.

The digital IC (DigIC) 191' functions as the primary interface between the processor 160' and the output current DAC circuitry 186', and its main function is to provide stimulus information to the output current DAC circuitry 186'. The DigIC 191' thus controls and changes the stimulus levels and sequences when prompted by the processor 160'. In an exemplary embodiment, the DigIC 191' comprises a digital application specific integrated circuit (digital ASIC).

With the basic structure of an implantable stimulator understood, focus now shifts to a detailed description of the battery protection and zero-Volt recovery aspects that are the focus of this disclosure. It is again worth noting that while particularly useful when implemented in implantable medical devices in which the problem of zero-Volt battery recovery is unique, the disclosed techniques can benefit any device or system in which zero-Volt recovery is beneficial. Thus, disclosure in the context of an implantable medical device should be understood as merely exemplary.

Figure 7:
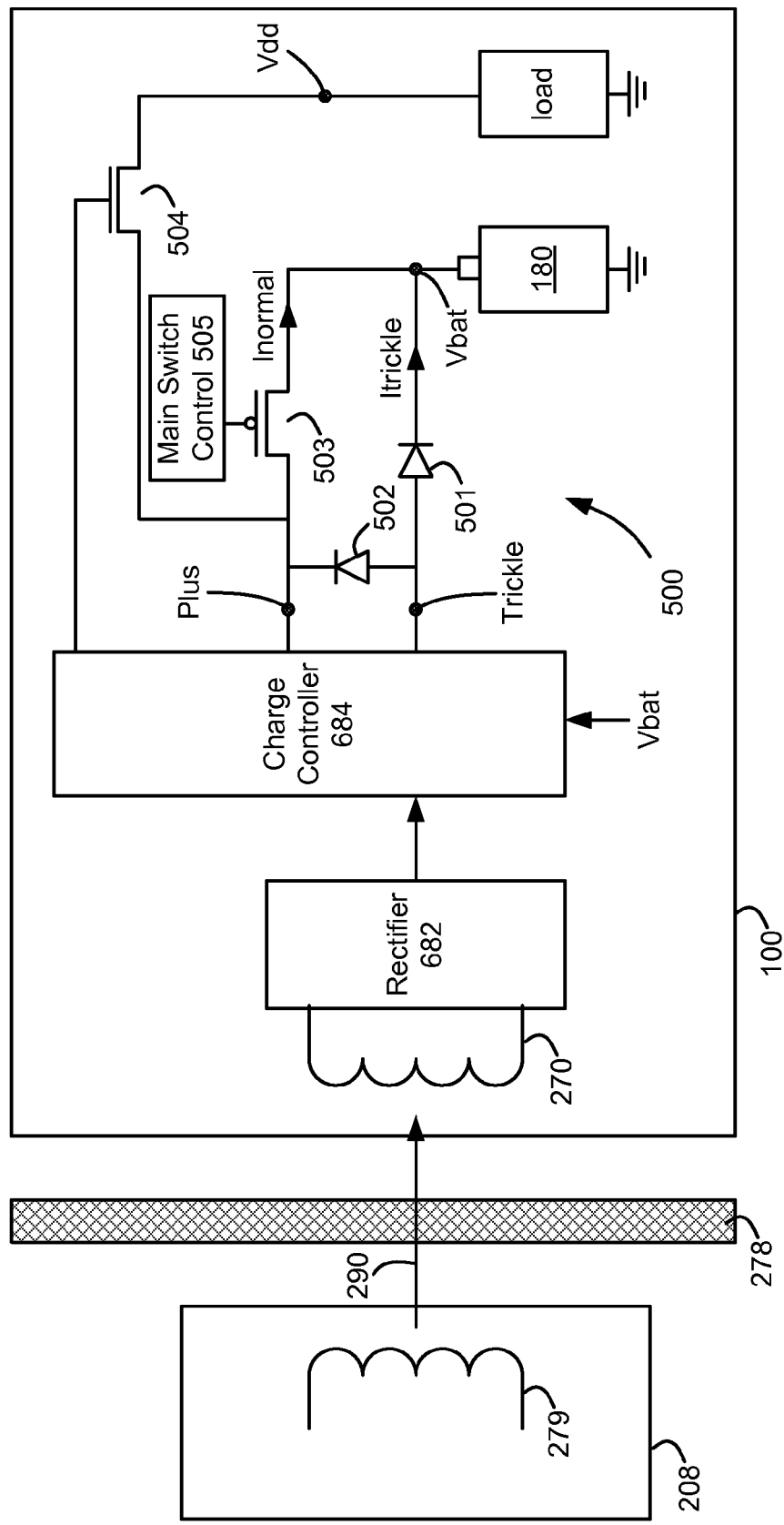
FIG. 7 is similar to the system illustrated in FIG. 1, but includes improved battery protection and zero-Volt recovery circuitry in accordance with an embodiment of the invention.

Improved battery protection and zero-Volt recovery circuitry 500 is shown in FIG. 7. Because many of the components are similar to components discussed earlier with respect to FIG. 1, they are labeled with the same element numerals, even if differing slightly in function as noted herein. Protection and zero-Volt recovery circuitry 500 is preferably formed on an integrated circuit, but may also comprise discrete components. Moreover, circuitry 500 may be integrated with the charge controller 684 or with other integrated circuits in the IPG 100, the level of integration and/or combination of functions being merely a design choice.

Briefly, protection and zero-Volt recovery circuitry 500 comprises in a preferred embodiment two distinct charging paths: one (designated by node "Trickle") for trickle charging, and another (designated by node "Plus") used for normal charging. At least one diode 501 (a passive device, unlike a transistor which must be actively gated) intervenes between node Trickle and the battery voltage, Vbat. (If more than one diode is used, they would be serially connected, although this is not shown in FIG. 7 for simplicity). A main switch 503 (preferably a P-channel MOS transistor) intervenes between node Plus and Vbat, which is controlled by a main switch control circuit 505, explained in further detail with respect to FIG. 8. Load switch 504 intervenes between node Plus and the load (designated by node "Vdd"), and is generally similar in function to the load switch of FIG. 1. However, it should be noted that coupling the battery 180 to the load requires that both switches 503 and 504 be closed, with main switch control 505 controlling the former, and the charge controller 684 for example controlling the latter. Additionally, a diode 502 intervenes between nodes Plus and Trickle. (In other embodiments, diode 502, like diode 501, may actually comprise a chain of serially-connected diodes, although FIG. 7 shows a single diode for simplicity).

Protection and zero-Volt recovery circuitry 500 basically supports and controls two operative modes: a charging mode and discharging mode.

The discharging mode is implicated when the battery 180 is coupled to the load, e.g., during normal operation, through main switch 503 and load switch 504. In discharge mode, the circuit 500 can sense a short circuit, i.e., from node Plus or Vdd to ground and/or excessive current draw, either of which evidences a problem with the IPG 100. When either condition is detected, the main switch 503 is turned off by main switch control circuit 505 to prevent the battery 180 from being drained, and will remain off until the external charger 208 turns it back on, a point discussed in further detail later.

Figure 1:
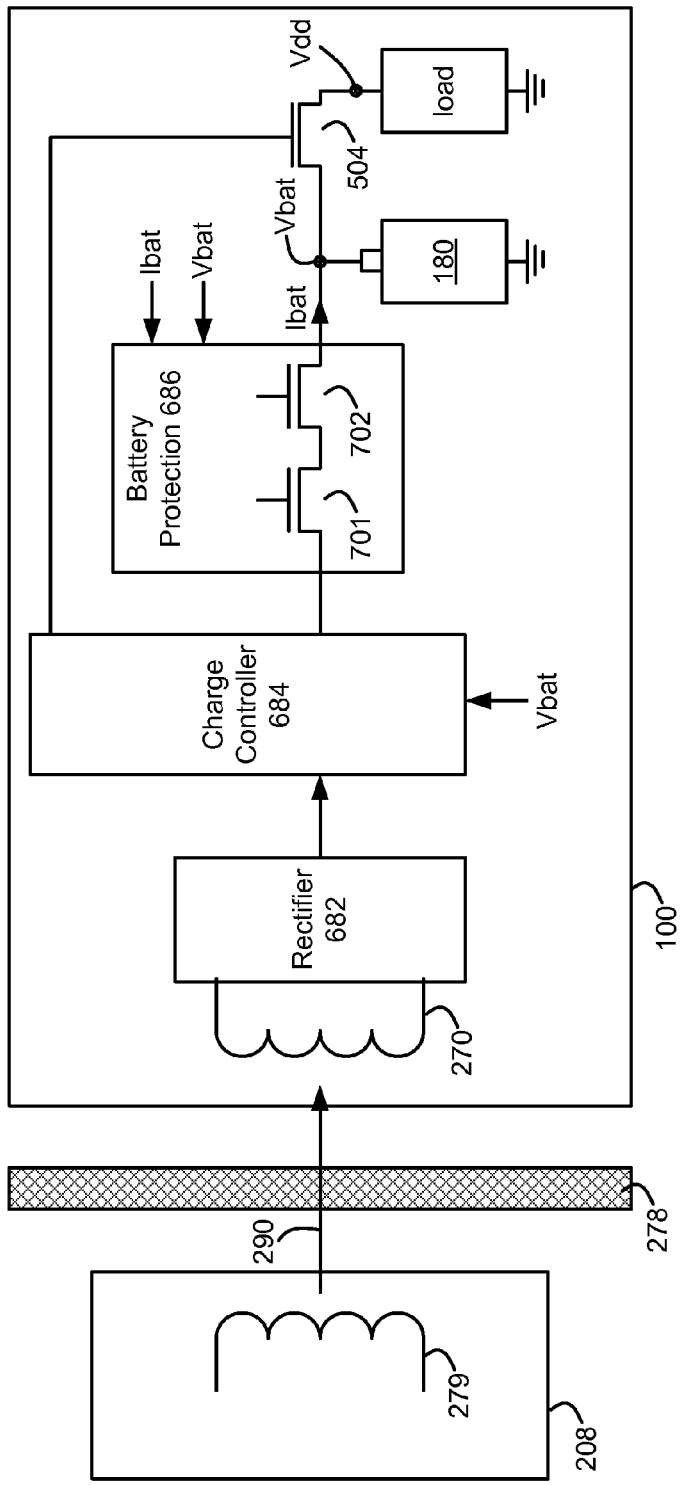
FIG. 1 illustrates a prior art system comprising an external charger for charging an implantable pulse generator (IPG), and shows the charge controller and battery protection aspects of the IPG.
Figure 2:
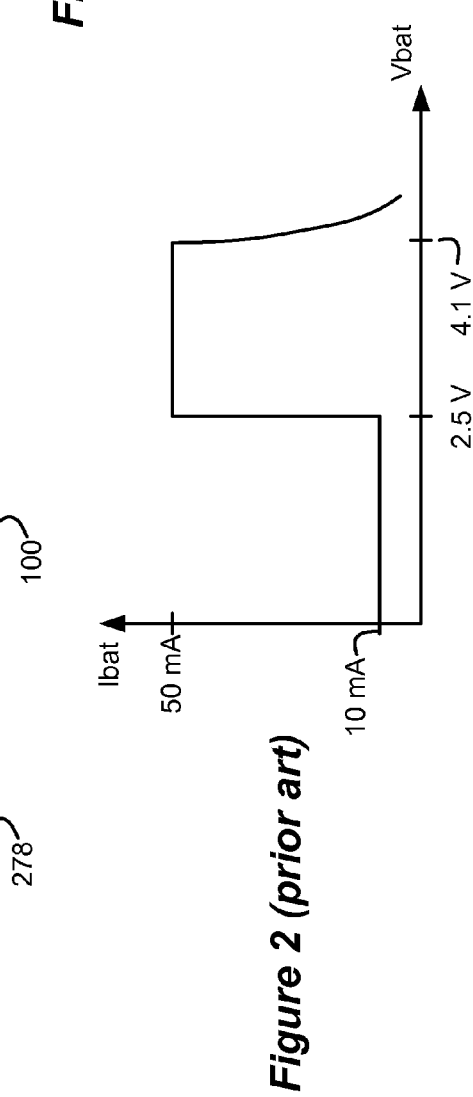
FIG. 2 graphically shows the relationship between battery voltage and battery current during charging of the battery as dictated by the charge controller of FIG. 1.

The charging mode can further be classified into two sub-modes: a trickle charging mode and a normal charging mode, similar to that discussed with respect to FIGS. 1 and 2. When the battery 180 voltage, Vbat, is sensed by the charge controller 684 to be less than the 2.5V, the circuit is in trickle charging mode. As will be seen, during trickle charging, current (Itrickle; approximately 10 mA) is passed from the charge controller 684 through node Trickle to charge the battery up to 2.5V. Once Vbat equals 2.5V, the charge controller 684 switches to the normal charging mode, thus passing a larger current (Inormal; approximately 50 mA) through node Plus to the battery. When the battery 180 is finally fully charged, the main switch 503 is turned off to isolate the battery 180 from the charge controller.

Figure 8:
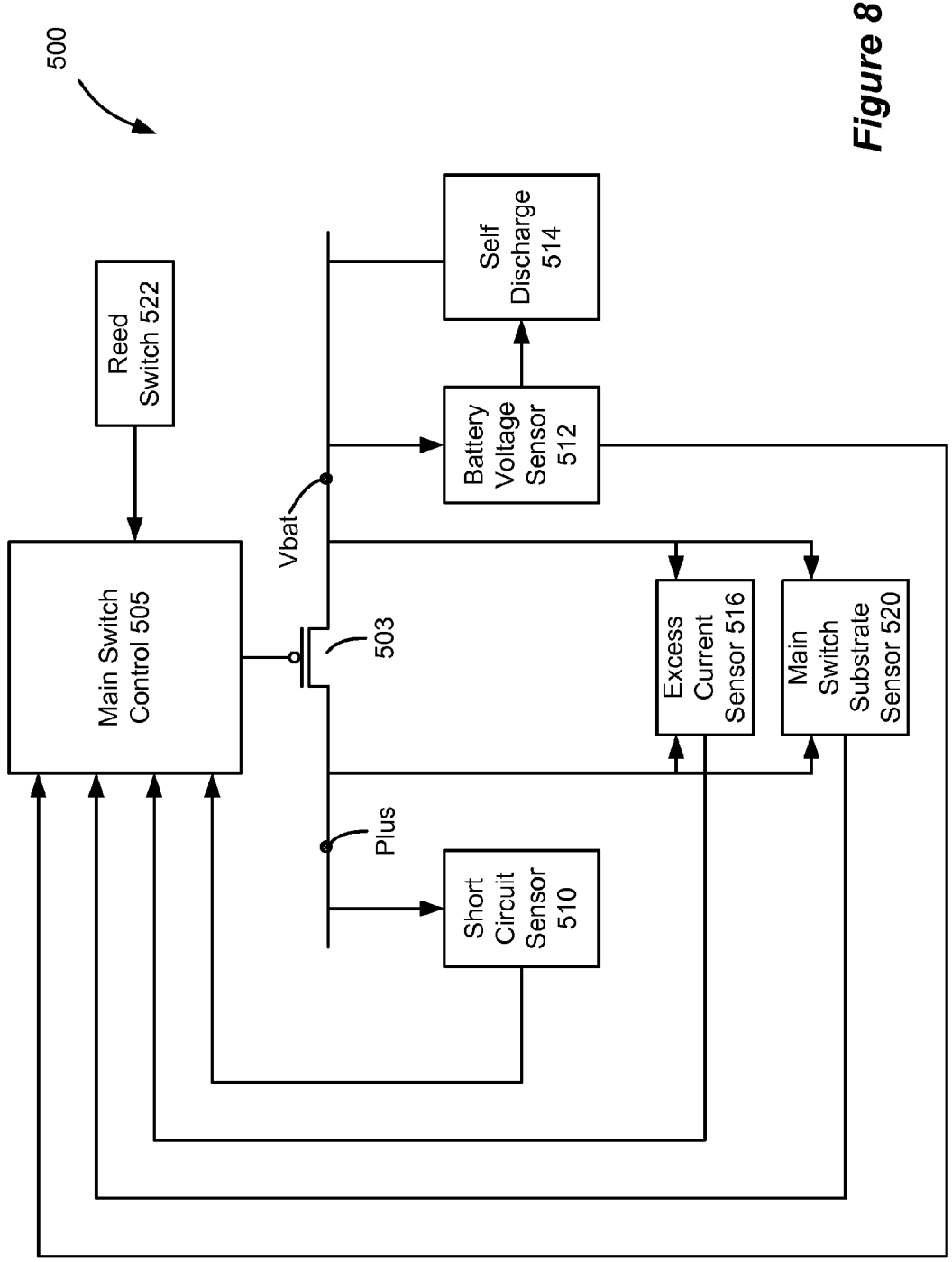
FIG. 8 illustrates the various sensors used in conjunction with the improved protection and zero-Volt recovery circuitry of FIG. 7.

As noted, the main switch 503 is controlled on and off by main switch control circuitry 505, and it is useful at this point to briefly explain how the logic in this circuitry 505 reacts to open and close the main switch 503. FIG. 8 thus show the various sensing circuits used to open and close the switch 503, not shown in FIG. 7 for clarity. While relevant to protection, one skilled in the art will realize that these various sensors may also be integrated with the charge controller 684.

Shown in FIG. 8 are four sensors: a short circuit sensor 510, a battery voltage sensor 512, an excess current sensor 516, and a main switch substrate sensor 520. Each sensor receives as input either the battery voltage, Vbat, or the voltage at node Plus as shown. Reed switch 522, preferably a discrete component separate from other integrated circuitry, can be used to freely disable the main switch 503, and thus terminate charging or discharging of the battery 180, for any number of other reasons.

Short circuit sensor 510 monitors the voltage at node Plus. If this voltage falls below an acceptable value (e.g., 0.8V), sensor 510 infers that a short circuit is present between Plus and ground (or between Vdd and ground if load switch 504 is on), and so directs the main switch control circuitry 505 to disable main switch 503, thus isolating the battery 180 to prevent it from draining. For safety reasons, should short circuit sensor 510 direct the main switch control circuitry 505 to disable the main switch 503, it is preferable that the main switch 503 stay permanently open until the external charger 208 (FIG. 1) is used to raise node Plus to an acceptable operating voltage. Of course, whether the external charger 208 will be capable of resetting main switch 503 ultimately depends on removal of the condition or "glitch" which caused the initial short circuit.

Battery voltage sensor 512 senses the voltage of the battery 180, Vbat, and can be used to inform the charge controller 684 of this value, e.g., so that the charge controller knows when to transition between trickle and normal charging. Battery voltage sensor 512 is also useful to assess whether Vbat is too high (e.g., greater than 4.2V), and if so, to activate self discharge circuit 514 to lower the voltage to a proper level. During normal operation, the battery voltage sensor 512 directs the main switch control 505 to close main switch 503 should Vbat be within normal operating parameters, e.g., between 2.5V and 4.2V, and otherwise directs control 505 to disable switch 503. The various voltage levels of interest to the battery voltage sensor 512 (e.g., 2.5V, 4.2V), may be trimmed to adjust their values to account for process variations via a multi-bit bus (not shown).

Excess current sensor 516, like short circuit sensor 510, is used to disconnect the battery 180 under conditions of high current draw. In a preferred embodiment, sensor 516 senses excessive current by measuring the voltage drop across the main switch 503, i.e., from node Plus to Vbat. Knowing the "on" resistance of the main switch 503 (preferably between 0.12 to 0.19 ohms when Vbat=3.6V), should the voltage drop suggest an excessive high current draw (e.g., greater than 400 mA), the short circuit sensor 510 directs the main switch control 505 to disable the main switch 503.

The main switch substrate sensor 520 monitors the polarity of current flow (charge or discharge) across the main switch 503 and ties the N-well of the main switch 315 to the higher of Plus or Vbat to prevent current loss to the substrate, as described further below.

The various sensors illustrated in FIG. 8 may be constructed using standard reference circuits, such as bandgap voltage reference circuits, voltage dividers, differential amplifiers, comparators, etc. Because such sensors circuits are well known and may take several different forms as one skilled in the art will appreciate, they are not discussed further.

Figure 9:
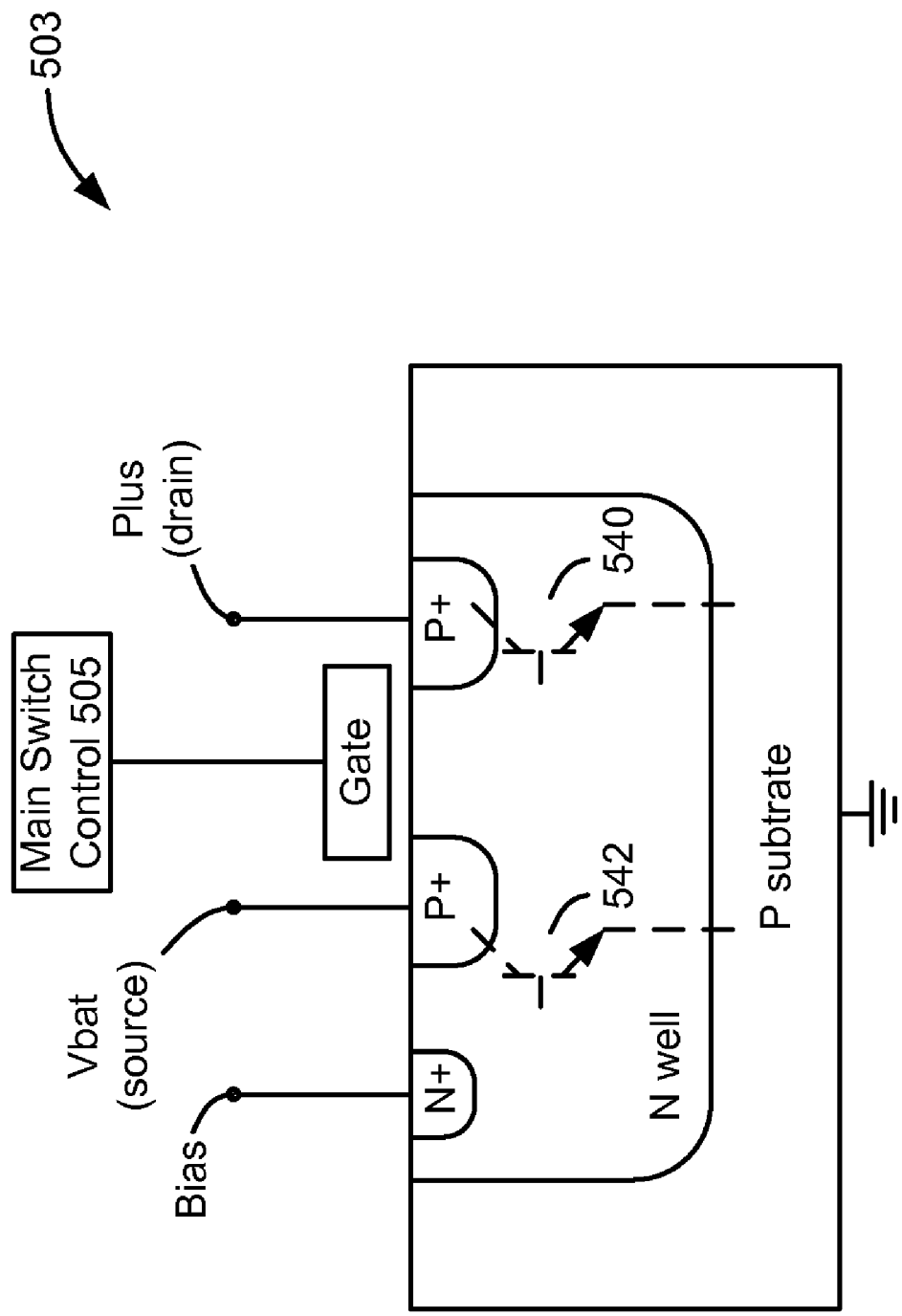
FIG. 9 illustrates the main switch used in the improved protection and zero-Volt recovery circuitry of FIG. 7, and shows parasitic current paths that can exist.

The main switch 503 is implemented with a PMOS transistor residing in an N well, such as is shown in cross-section in FIG. 9. It should be noted that the source and drain regions of the main switch 503 (which are otherwise symmetrically fabricated as one skilled in the art will appreciate, and hence arbitrarily named in FIG. 9) will be subject to different voltages depending on whether the battery 180 is being charged or discharged. For example, during normal charging, node Plus is brought high due to biasing from the charge controller 684; while being discharged, Vbat is brought relatively high by the battery 180.

Since the source and drain regions of the main switch 503 are subject to these different voltage polarities, the N well potential (node "Bias" in FIG. 9) is tied to the higher of potential of the source or drain of main switch 503 at all times, rather than simply always having the N well biased to Vbat as would be more typical for a PMOS transistor. This prevents unwanted current draw to the substrate.

To illustrate this problem, consider normal charging of battery. When charging commences, the provision of current (i.e., voltage) at node Plus may be relatively high when compared with Vbat, i.e., depending on Vbat's current level of charge. If Vbat is coupled to the N well at node Bias, a parasitic PNP bipolar transistor (540; FIG. 9) could turn on, with the result that current meant to trickle charge the battery 180 would be routed to the substrate of the main switch 503. Such inadvertent siphoning of the current would at least slow the charging of the battery 180, or if significant, could prevent charging of the battery 180 altogether. However, this problem is not simply fixed by tying the N well (Bias) to node Plus, because during discharging, the parasitic effect could be realized at the other of the source/drain of the switch 503: that is, during discharge, Vbat could be higher than Plus, which could turn on the parasitic PNP bipolar transistor at the other terminal (542; FIG. 9), causing current otherwise useable by the load to be inadvertently drained to the substrate. To address this problem, as noted, the N well (node Bias) is biased to the higher of the source or drain nodes of main switch 503 via a polarity control circuit, such as the main switch substrate sensor 520 discussed above (see FIG. 8). The design of such a polarity control circuit is easily made by those of skill in the art and can be made in many different ways.

With this overview of the protection and zero-Volt recovery circuitry 500 in hand, attention can know be focused on how the circuit 500 operates to protect and charge the battery 180, even from a completely zero-Volt state.

In this regard, and as noted earlier, note from FIG. 7 that the trickle charging path (node Trickle; current Itrickle) is separated from normal charging path (node Plus; current Inormal). Zero-Volt recovery is the driving factor for separating these two charging paths. By separating the Trickle and Plus nodes, the trickle charging current (Itrickle) can be prevented from flowing into the Plus node, and hence bipolar transistor parasitics in the main switch 503 are not implicated. At the same time, because the trickle current bypasses the main switch 503, potential uncertainty in the status of the switch at low voltages is of little concern.

However, what is of concern is the possibility of current leakage through node Plus to the substrate. This is alleviated in one embodiment by holding node Plus at a suitable voltage level during trickle charging. Specifically, in a preferred embodiment, during trickle charging, node Plus is tied to Vbat. This is accomplished in one embodiment through the use of diode(s) 502. The function of diode(s) 502 is to match the voltage drop across diode(s) 501 during trickle charging to keep the voltage at Plus the same as Vbat so that trickle charge current does not leak to the substrate through switch 503. In other words, if 502 were not present, the voltage at Plus could be below the battery and 503 could leak to the substrate.

Although diodes 501 and 502 are shown as single diodes in FIG. 7, different numbers of diodes can be used. In a preferred embodiment, two diodes in series are used for diodes 501 and 502. Moreover, it should be realized that diodes 501, 502 can be realized as transistors in which one of the source and drain are tied to the substrate (well), as is well known. As such, "diode" as used herein should be understood as including such structures, and any other structures capable of one-way current transmission.

With Plus held to Vbat during trickle charging, even if the N well is likewise biased to Vbat, the parasitic bipolar transistor 540 (FIG. 9) cannot turn on due the zero-Volt potential difference between the Plus and the well. Moreover, pursuant to this biasing scheme, all junction nodes of the main switch 503 are held to the same potential, i.e., source=drain=N well=Vbat. The result is that no current can flow through main switch 503, regardless of whatever potential is present on the gate of the transistor. That being said, when it is desired for the main switch 503 to be off, it may still be preferable to bias the gate of main switch 503 to the higher of the two voltages apparent at its source and drain regions, just as the N well is biased as explained earlier. (Similar circuitry could be used for both of these functions). This even further helps to ensure that the PMOS main switch 503 will not conduct during trickle charging.

Thus, in contrast to the circuit of FIG. 1 as discussed in the Background, low values for Vbat, which affected the ability to turn on transistors 701, 702, become irrelevant, and zero-Volt recovery of the battery is realized through node Trickle. This is true even if the various sensors, such as battery voltage sensor 512 (FIG. 8), cannot operate reliably at lower values of Vbat, because trickle charging can reliability occur regardless of what such sensors would otherwise indicate to the main switch control 505, and how the main switch control 505 would bias the gate of the main switch 503. With the Plus node effectively prevented from drawing current during trickle charging, trickle charging can be accomplished by having the charge controller 684 providing a significantly high bias to node Trickle to overcome the forward threshold on diode 501 to produce the desired trickle current, Itrickle.

Once the battery 180 has been trickled charged as just described, eventually Vbat will raise to a level at which normal charging can take place, e.g., at 2.5V. By way of review, monitoring of Vbat for this cross-over condition is the function of battery voltage sensor 512 of FIG. 8, which, like main switch control 505 will start functioning reliably once Vbat is charged to a suitably high level (e.g., 2.0V). Thus, whereas during trickle charging the gate voltage of main switch 503 was irrelevant because the voltage conditions in the source, drain, and well prevented current flow, during normal charging, voltages have been charged to a suitable level that the main switch control 505 and other sensors reporting to it can now reliably turn on the switch 503 to permit the flow of current (Inormal) from the charge controller 684 to node Plus, and ultimately to the battery 180. Because the voltage at node Plus will be relatively high during normal charging, diode 502 will be reversed-biased, thus preventing the flow of current to node Trickle.

In summary, protection and zero-Volt recovery circuitry 500 is capable of both protecting the battery, and charging the battery 180 even from a zero-Volt condition. Protection is present by the ability to isolate the battery 180 from both the load via load switch 504 and from the charge controller via main switch 503 and via diode 501 (which will prevent battery discharge back to the charge controller 684). Such protection does not hamper the circuitry 500 from being charged. Instead, through the provision of two separate charging paths, Plus and Trickle, the battery can be charged through one path (Trickle) without concern that the protection circuitry will inhibit low-level charging when the battery is at low voltages. Once suitable charged, the other path (Plus) is used to charge the battery through the protection circuitry (e.g., main switch 503) to nominal voltages. Thus, the battery and load are protectable from adverse voltage and current conditions, and the battery can be fully recovered. As noted earlier, this is especially important when the circuitry 500 is incorporated in an implantable medical device such as an IPG 100, for failure to recover a fully depleted battery might otherwise warrant surgical extraction of the device.

While the invention herein disclosed has been described by means of specific embodiments and applications thereof, numerous modifications and variations could be made thereto by those skilled in the art without departing from the literal and equivalent scope of the invention set forth in the claims.

What is claimed is:

1. A protection and recovery circuit for an implantable medical device, comprising:
a rechargeable battery having a threshold voltage;
at least one first diode;
a first switch;
charging circuitry for issuing a first charging current from a first node along a first charging path, and for issuing a second charging current from a second node along a second charging path, wherein the first and second nodes are separated,
the first charging current for charging the battery through the at least one first diode, wherein the first charging path is active to charge the battery from zero volts when a voltage of the battery is below the threshold voltage; and
the second charging current for charging the battery through the first switch; and
a controller for closing the first switch when a voltage of the battery is above the threshold voltage.

2. The circuit of claim 1, further comprising a load, wherein the load is coupled to the second charging path such that the first switch is active to couple the battery to the load.

3. The circuit of claim 2, further comprising a second switch between the first switch and the load for decoupling the load.

4. The circuit of claim 1, further comprising at least one second diode between the first charging path and the second charging path.

5. The circuit of claim 1, wherein the first switch comprises a PMOS transistor.

6. The circuit of claim 5, further comprising a polarity control circuit, and wherein a well of the PMOS transistor is biased by the polarity control circuit to a higher of a source or a drain of the PMOS transistor.

7. The circuit of claim 5, further comprising a polarity control circuit, and wherein a well of the PMOS transistor is biased by the polarity control circuit to the battery voltage.

8. A protection and recovery circuit for an implantable medical device, comprising:
a rechargeable battery having a threshold voltage;
at least one first diode;
a first switch;
a charge controller with a first output and a second output for charging the rechargeable battery;
a first charging path between the first output of the charge controller and a terminal of the battery for charging the battery through the at least one first diode, wherein the charge controller controls the first charging path to be active to charge the battery from zero volts when the charge controller determines that a voltage of the battery is below the threshold voltage; and a second charging path between the second output of the charge controller and the terminal of the battery for charging the battery through the first switch, wherein the charge controller controls the second charging path to be active to charge the battery when the charge controller determines that a voltage of the battery is above the threshold voltage.

9. The circuit of claim 8, further comprising a switch control circuit for controlling the first switch to deactivate the second charging path.

10. The circuit of claim 8, further comprising a load, wherein the load is coupled to the second charging path such that the first switch is active to couple the battery to the load.

11. The circuit of claim 10, further comprising a second switch between the first switch and the load for decoupling the load.

12. The circuit of claim 8, further comprising at least one second diode between the first charging path and the second charging path.

13. The circuit of claim 8, wherein the first switch comprises a PMOS transistor.

14. The circuit of claim 13, further comprising a polarity control circuit, and wherein a well of the PMOS transistor is biased by the polarity control circuit to a higher of a source or a drain of the PMOS transistor.

15. The circuit of claim 13, further comprising a polarity control circuit, and wherein a well of the PMOS transistor is biased by the polarity control circuit to the battery voltage.

16. The circuit of claim 13, wherein a well of the PMOS transistor is biased to a voltage output by the charge controller on the first charging path.

* * * * *